United States Patent
Govindaraj et al.

(10) Patent No.: US 12,395,018 B2
(45) Date of Patent: Aug. 19, 2025

(54) CONTROL SYSTEM FOR WIRELESS POWER CHARGING AND ALIGNMENT

(71) Applicant: Verily Life Sciences LLC, South San Francisco, CA (US)

(72) Inventors: Arvind Govindaraj, Mountain View, CA (US); Peng Cong, Burlingame, CA (US)

(73) Assignee: Verily Life Sciences LLC, Dallas, TX (US)

( * ) Notice: Subject to any disclaimer, the term of this patent is extended or adjusted under 35 U.S.C. 154(b) by 792 days.

(21) Appl. No.: 17/423,990

(22) PCT Filed: Jan. 21, 2020

(86) PCT No.: PCT/US2020/014362
§ 371 (c)(1),
(2) Date: Jul. 19, 2021

(87) PCT Pub. No.: WO2020/159748
PCT Pub. Date: Aug. 6, 2020

(65) Prior Publication Data
US 2022/0103023 A1    Mar. 31, 2022

Related U.S. Application Data

(60) Provisional application No. 62/798,055, filed on Jan. 29, 2019.

(51) Int. Cl.
*H02J 50/90* (2016.01)
*A61N 1/378* (2006.01)
(Continued)

(52) U.S. Cl.
CPC ............ *H02J 50/90* (2016.02); *A61N 1/3787* (2013.01); *H02J 7/00714* (2020.01);
(Continued)

(58) Field of Classification Search
CPC .. H02J 50/90; H02J 50/80; H02J 50/10; H02J 50/20; H02J 7/007182; H02J 7/00714; A61N 1/3787
(Continued)

(56) References Cited

U.S. PATENT DOCUMENTS

| 9,446,254 B2 | 9/2016 | Ozawa et al. |
| 9,849,298 B2 | 12/2017 | Ozawa et al. |

(Continued)

FOREIGN PATENT DOCUMENTS

| CN | 105264736 A | 1/2016 |
| WO | 2018136885 | 7/2018 |

OTHER PUBLICATIONS

European Application No. 20748951.9, "Extended European Search Report", Sep. 14, 2022, 7 pages.

(Continued)

*Primary Examiner* — Nathaniel R Pelton
(74) *Attorney, Agent, or Firm* — Kilpatrick Townsend & Stockton LLP

(57) ABSTRACT

A system for wirelessly charging an implantable device is described. The system may include an estimation device or component that estimates a field strength at a receiving coil of the implantable device based on available electrical signals within the implantable device. The system may also include a control system for varying a strength of a charging field produced by a charger. The system may also be used to align a wireless charger with the implantable device for charging a battery of the implantable device. Methods and devices for implementing the charging system are also described.

35 Claims, 9 Drawing Sheets

(51) Int. Cl.
    *H02J 7/00*     (2006.01)
    *H02J 50/10*     (2016.01)
    *H02J 50/20*     (2016.01)
    *H02J 50/80*     (2016.01)

(52) U.S. Cl.
    CPC ........ *H02J 7/007182* (2020.01); *H02J 50/10* (2016.02); *H02J 50/20* (2016.02); *H02J 50/80* (2016.02)

(58) Field of Classification Search
    USPC .......................................................... 320/108
    See application file for complete search history.

(56) References Cited

U.S. PATENT DOCUMENTS

| | | |
|---|---|---|
| 9,968,791 B2 | 5/2018 | Aghassian |
| 2014/0074185 A1* | 3/2014 | Fell ...................... A61N 1/3787 |
| | | 320/108 |
| 2015/0100109 A1 | 4/2015 | Feldman et al. |
| 2015/0174416 A1 | 6/2015 | Angara et al. |
| 2015/0196764 A1* | 7/2015 | Marnfeldt .......... A61N 1/36128 |
| | | 607/59 |
| 2017/0040841 A1 | 2/2017 | Ridler et al. |
| 2017/0069969 A1* | 3/2017 | Black ..................... H02J 50/60 |
| 2017/0202467 A1 | 7/2017 | Zitnik et al. |
| 2017/0281944 A1 | 10/2017 | Khalil et al. |

OTHER PUBLICATIONS

International Application No. PCT/US2020/014362, International Search Report and Written Opinion, mailed May 18, 2020, 14 pages.
International Application No. PCT/US2020/014362, Invitation to Pay Additional Fees and, Where Applicable, Protest Fee, mailed Mar. 17, 2020, 2 pages.
Europe Appl. No. 20748951.9, Office Action, Mar. 11, 2024, 3 pages.
China Appl. No. 202080011572.3, Office Action, Jun. 10, 2025.

* cited by examiner

CONTROL SYSTEM FOR WIRELESS POWER CHARGING AND ALIGNMENT

CROSS-REFERENCE TO RELATED APPLICATIONS

This application claims priority to U.S. Provisional Patent Application No. 62/798,055, titled "Control System for Wireless Power Charging and Alignment," filed Jan. 29, 2019, which is hereby incorporated by reference in its entirety.

BACKGROUND

Implantable devices, such as devices implanted in the body of an individual or other living being, may be used for various functions. For example, a neuromodulation device may be implanted to treat a wide range of disorders. As another example, a brain-computer interface may be implanted to augment and/or repair various cognitive and sensory-motor functions. Yet another example is a micro sensor for sensing physiological parameters of an individual. These and other implantable devices may include various subsystems for collecting data, providing outputs based on collected data, performing calculations, and/or carrying out various instructions. Once an implantable device is placed within a user, its battery cannot be easily replaced.

Various techniques and systems exist for powering an implantable device. One technique includes providing power to an implantable device through wireless power transfer using electromagnetic waves. Most conventional systems use near-field inductive coils for charging the battery of an implantable device.

SUMMARY

Various examples are described relating to charging and alignment of wireless chargers with implantable devices, systems for charging and alignment of wireless chargers with implantable devices, and methods for charging and alignment of wireless chargers with implantable devices. The methods, systems, and examples described below relate to closed-loop charging and alignment of an implantable device with a wireless charger using an electromagnetic ("EM") field.

In an example, a system is described. The system includes an implantable device having a field estimator to estimate a present or an estimated EM field value and a target EM field value or intensity, related to the strength of a charging field at the implantable device, needed to charge a battery of the implantable device. The implantable device also includes a communication device to transmit the present and target EM field values to a charger. The system also includes a wireless charger including a communication device, an EM field driver, and a controller. The communication device communicates with the implantable device and receives the EM field values. The controller uses the EM field values to alter or control the EM field driver. The controller is designed to cause the EM field driver to adjust the charging EM field until the present or experienced EM field value and the target EM field value at the implantable device match or are as close as reasonably possible.

In another example, a method is described. The method includes measuring or detecting a set of electrical parameters or values within the implantable device, estimating a present EM field value based on the set of electrical parameters, estimating a target EM field value for charging a battery of the implantable device based on the set of electrical parameters, and controlling EM field driver of a wireless charger based on the present EM field value and the target EM field value. In some examples, the present EM field value, or present estimation value, and the target EM field value, or target EM field intensity, comprise field information related to the EM field.

In yet another example, a method is described for aligning a wireless charger with an implantable device. The method includes producing a beacon or alignment EM field from an EM field driver at a wireless charger, receiving or detecting the beacon EM field at the implantable device, determining that the wireless charger can produce a charging EM field, and generating a notification related to the determination. The method also includes determining that the wireless charger can produce the charging EM field based on a predetermined maximum electrical parameter of the charger, such as a predetermined maximum voltage, the detected or present beacon EM field value at the implantable device, a target EM field value for charging, and a beacon electrical parameter of the charger corresponding to the beacon EM field.

In yet another example, a method is described for estimating a EM field at an implantable device. The method includes determining a voltage and a current at a rectifier of an implantable device. The voltage and the current are compared or used in connection with an electrical model, or a simplified electrical model, of the implantable device—the electrical model representing a relationship between the rectifier voltage and current and a detected or experienced EM field value. The method also includes estimating a present or experienced EM field value, a scalar indicating the strength of the EM field at the implantable device, based on the comparison of the current and voltage at the rectifier to the electrical model. The method further includes transmitting the present EM field value to a wireless charger or a controller associated with a wireless charger.

The illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
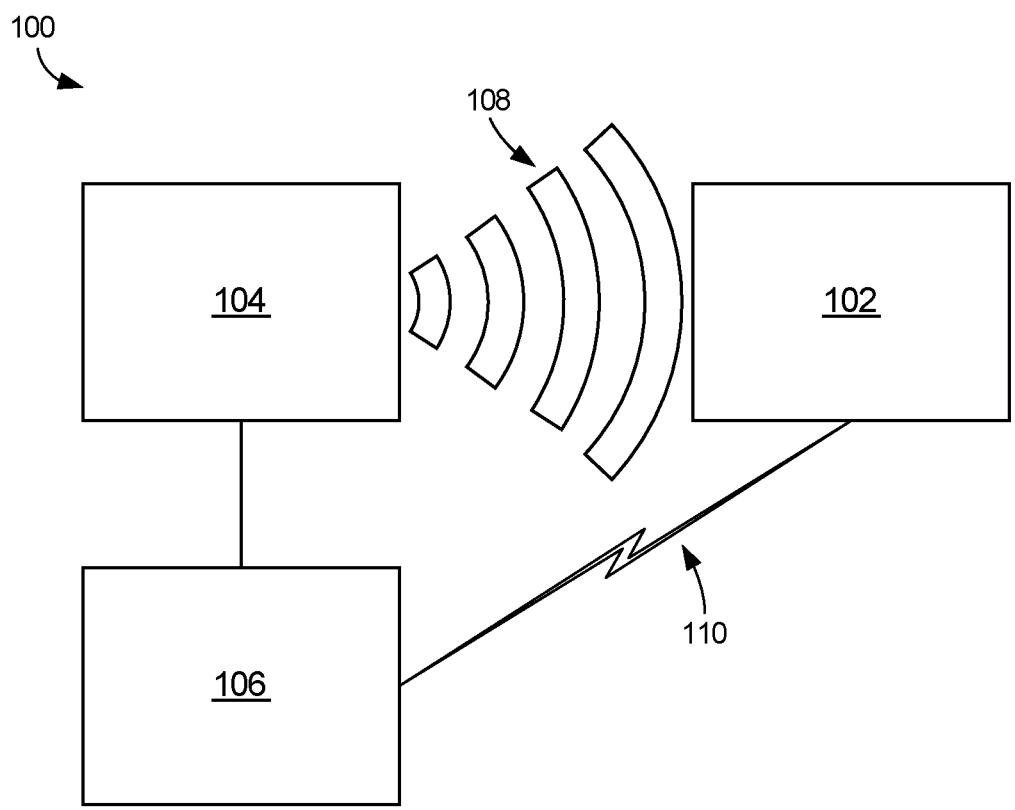
FIG. 1 illustrates a wireless charging system for charging an implantable device, according to at least one example.

Examples are described herein in the context of wireless charging and power supply to an implantable device. Those of ordinary skill in the art will realize that the following description is illustrative only and is not intended to be in any way limiting. For example, the control and alignment systems described herein can be used with a variety of wireless chargers, though for convenience an inductive charging device is described. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Implantable devices include mechanical, electrical, and pharmaceutical stimulators and typically use electrochemical cells or batteries for energy to cause the needed stimulation. Rather than requiring surgery to remove and replace expired batteries, wireless charging systems can supply energy to the implantable device, equipped with a charger, to recharge the batteries. In wireless charging systems, a charger or energy source includes a charging coil configured to inductively transfer wireless energy by inducing voltage in a receiving coil of an implantable device. Wireless charging, and specifically inductive charging, typically requires a small distance, e.g., a few centimeters, between the charger and the device to be charged, but allows an implantable device to be recharged without surgery or removal from the user's body. Because of the short-range charging distance, and since charging is faster and more efficient when the wireless charger and the implantable device are properly aligned, it is advantageous to properly align the two when charging.

The system described herein provides closed-loop wireless charging to an implantable device. The closed-loop wireless charging system includes an implantable device, a wireless charger such as an inductive charger described above, and a controller connected to the wireless charger. In some examples, the controller is included within the same unit as the wireless charger. The implantable device estimates the strength of the received electromagnetic ("EM") charging field using known electrical parameters or signals within the implantable device. For example, the implantable device includes a rectifier to rectify the received EM energy and the implantable device estimates the strength of the EM field by using a model of the implantable device and the voltage and current at the rectifier.

In an illustrative example, an implantable device is configured to estimate the strength or level of an EM field at the implantable device using electrical signals available within the implantable device, such as voltage and current values through a rectifier of the implantable device. The field estimator estimates not only a present or an actual/detected EM field value, but also estimates a target EM field value for charging a battery of the implantable device. The field estimator calculates the target EM field, representing a target strength of the charging EM field such as a charging EM field value, at the receiving coil of the implantable device value based on a present battery voltage or charge and other factors such as a charging overhead and a charging current value. The implantable device also includes a communication device, which can be used to convey the present and the target EM field values from the implantable device to a controller (e.g., a component of a wireless charger). The controller is equipped to receive the present and the target EM field values. Using these present and the target EM field values, the controller controls an EM field driver to produce an EM field that results in a present EM field value that matches the target EM field value. The controller limits, controls, or transmits a signal instructing the wireless charger to control at least one electrical parameter of the EM field driver to influence and control the EM field produced by the EM field driver.

In a second illustrative example, a system and method for aligning a wireless charger with an implantable device, after being implanted in a user is described. The system and method involve a user placing the wireless charger near a location of the implantable device and moving the wireless charger in response to notifications or feedback from the system to align the wireless charger with respect to the implantable device for charging. The implantable device includes a field estimator as described above to estimate the present and target EM field values based on the current and voltage values within the implantable device, and transmits the present and target EM field values to the controller. The controller and/or the wireless charger contains processors, microprocessors, other circuitry, and/or software to determine whether, based on the present level of current supplied to the EM field driver and the present EM field value, the EM field driver can produce an EM field that will result in a present EM field value matching the target EM field value without exceeding a threshold current level at the EM field driver. If the controller determines it can deliver the required EM field, then a notification is generated indicating that the wireless charger and implantable device are aligned for charging. If the controller determines that the EM field cannot be produced, then a user may continue moving the wireless charger searching for a location where the controller determines it can deliver the required charging EM field. In any event, the controller is also configured to provide a notification, after a predetermined period of time passes without aligning the wireless charger, of a location where the wireless charger can come closest to meeting the field criteria for charging.

The examples described herein provide benefits for wireless charging systems for implants. In some examples, controlling the wireless charger can result in power savings because the wireless charger and wireless field driver may be controlled to produce EM filed having just enough strength to charge the implantable device battery without wasting additional energy. An additional benefit of the controlled wireless charger is a reduction in heat buildup as a result of the EM field inducing eddy currents in a metal canister of the implantable device. The examples, systems, and methods described herein also maintain a compact implantable device footprint or size while providing additional benefits and efficiency, some of which has been described above. The field estimator and controller may use or connect directly to the electrical components of the implantable device to detect signals and determine estimated and target EM field values without the need to introduce or add additional voltage or current sensors, though in some examples additional sensors such as current and voltage detection circuits may be included.

These illustrative examples are given to introduce the reader to the general subject matter discussed herein and the disclosure is not limited to these examples. The following sections describe various additional non-limiting examples of control and alignment systems or methods for wirelessly charging implantable devices.

Referring now to FIG. 1, a system 100 for wirelessly charging an implantable device 102 using a charger controller 106 and a wireless charger 104 is shown. The implantable device 102 is in communication over a communication channel 110 with the charger controller 106. The communication channel 110 between the implantable device 102 and the charger controller 106 can include a short-range communication over short-range communication channels, such as Bluetooth or Bluetooth Low Energy (BLE) channel. In some examples, communicating using a short-range communication such as BLE channel can provide advantages such as consuming less power, being able to communicate across moderate distances, being able to detect levels of proximity, achieving high-level security based on encryption and short ranges, and not requiring pairing for inter-device communications. The implantable device 102 may already be configured to communicate with an external device, and the communication channel 110 may be the communication channel typically used by the implantable device.

The charger controller 106 can be a device separate and distinct from the wireless charger 104, or may be built into the wireless charger 104. In any case, the charger controller 106 is able to communicate with the wireless charger 104 to control an EM field 108 produced by the wireless charger 104. As an example, the EM field 108 is an EM field produced by an EM field driver, or coil, within the wireless charger 104.

The implantable device 102 communicates with the charger controller 106 via the communication channel 110. For example, the implantable device 102 can transmit data and information relating to its operation (e.g., electrical signals of the implantable device 102) to the charger controller 106. The charger controller 106 can use the data and information to control and/or adjust the EM field 108, e.g., to reduce wasted energy, prevent heating of the implantable device, and ensure proper alignment and charging of a battery within the implantable device 102.

Figure 2:
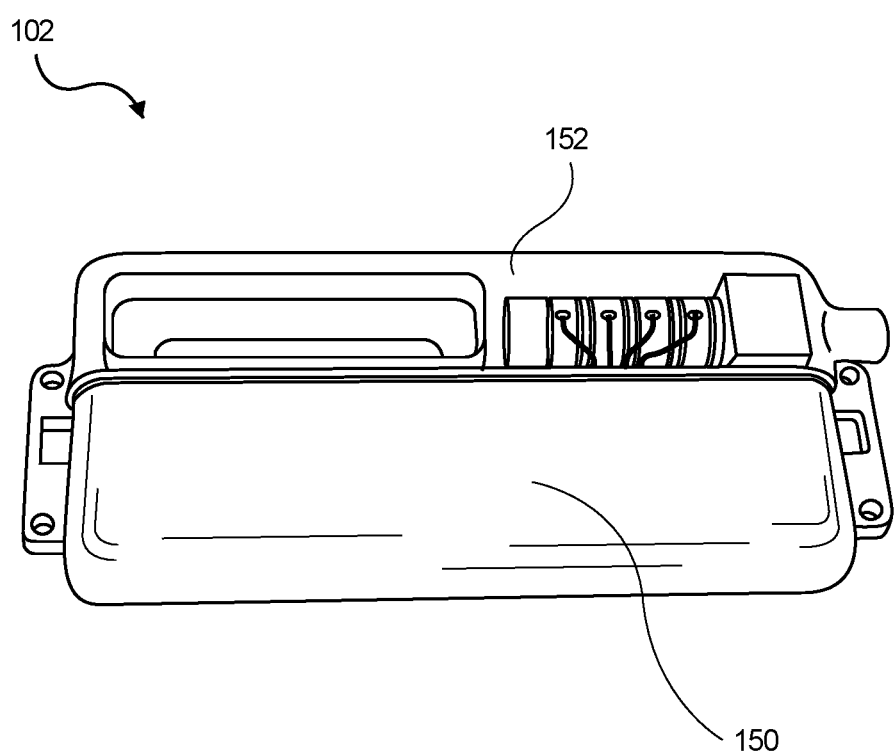
FIG. 2 illustrates an implantable device, according to at least one example.

FIG. 2 shows an example of the implantable device 102 for use with the systems and methods described herein, according to at least one example. The implantable device 102 includes a canister 150 containing electronics, processors, circuitry, and other components for carrying out the purpose of the implantable device 102. For a neuromodulation device, the electronics, processors, circuitry, and other components inside the canister 150 are configured to deliver electrical or pharmaceutical agents or stimuli to a target area in a user. In some examples, the canister 150 shields the components disposed therein. As such, the canister 150 can be formed from or include a metal or other shielding material or arrangement, e.g., a wire mesh that may provide a Faraday cage. A charging coil, communication device, and other components which must remain unshielded can be arranged within a container 152, which can be formed from a non-metallic material such as plastic.

In conventional implantable devices and charging systems, electrical interference and/or overheating can occur when a charger provides a more powerful charging field than is needed to charge the implantable device. For example, an EM field produced by a wireless charger will produce eddy currents in the canister 150 of an implantable device and can heat the canister causing discomfort to the user and potentially damage to the implantable device.

The systems described herein control the charger in a way that conserves energy resources and uses them efficiently. This is achieved, at least in part, by the charger controller 106 controlling the wireless charger 104 to produce a EM field 108 that is considerate of the conditions in which the implantable device 102 is present. Because of this, an intensity of the EM field 108 is selected that is sufficient to charge the battery of the implantable device 102 and mitigates or eliminates energy waste and losses and prevents heating the canister 150.

Because the implantable device 102 is intended to be implanted inside the body of a user, it is beneficial to keep the size and/or the footprint of the implantable device 102 as small as possible. This size limitation otherwise excludes the use or inclusion of additional components to perform tasks such as magnetic or charging field detection should be because of the associated increase in size or footprint of the implantable device 102. For example, a EM field detector can be implemented to accomplish field strength measurement, and relayed to the charger controller 106 for controlling the wireless charger 104 and EM field 108, however, the additional components, such as the field detector, occupy space and would increase the footprint of the implantable device 102. The systems and methods described herein resolve the footprint problem and do not increase the size of the implantable device 102 by using electrical signals contained within the implantable device to estimate the EM field strength based on an electrical model of the implantable device 102.

Figure 3:
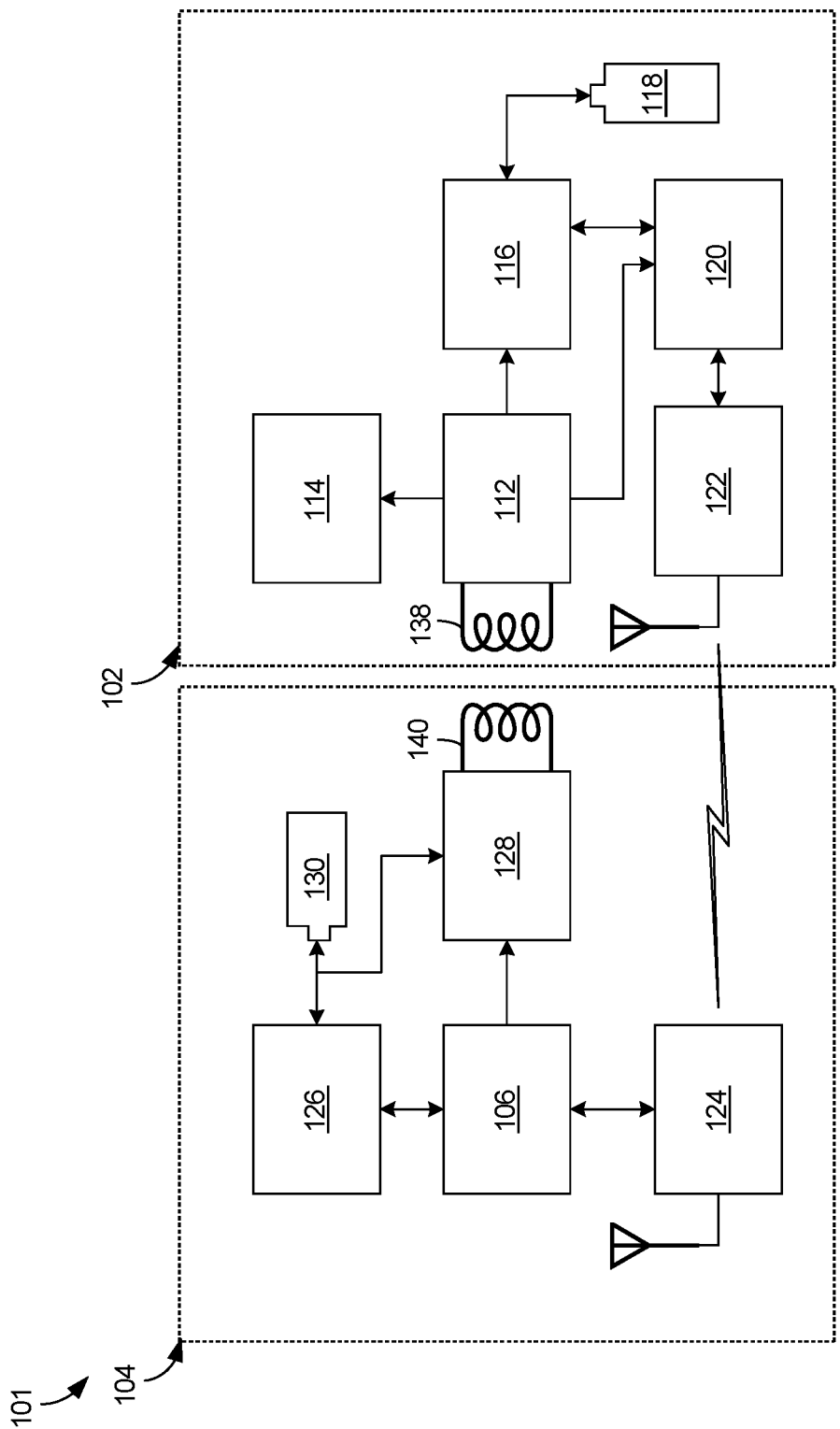
FIG. 3 illustrates a block diagram depicting a wireless charging system, according to at least one example.

FIG. 3 shows a diagram of an example wireless charging control system 101 including the implantable device 102 and the wireless charger 104, according to at least one example. Generally, the implantable device 102 includes components for a typical neuromodulation device as well as power, charging, and communication systems. Generally, the wireless charger 104 includes a power source, control systems, communication systems, a EM field driver, and an inductive coil for producing a charging field.

The implantable device 102 includes a receiving coil 138, a rectifier 112, an overvoltage protection shunt 114, a linear battery charger 116, a battery 118, an implantable device controller 120, and an implantable device communication device 122. The receiving coil 138 receives a transmitted charging field such as a EM field, which induces a current in the receiving coil 138. The rectifier 112, which is electrically connected to the receiving coil 138, receives an alternating current induced in the receiving coil 138 and converts the current into a direct current which is better suited for charging the battery 118 of the implantable device 102. The rectifier 112 may include a number of components in a rectifying circuit such as those shown and described with respect to FIG. 5 below.

An overvoltage protection shunt 114 is provided for instances where an input voltage exceeds a maximum or threshold voltage at the rectifier 112. This may occur due to an excessively powerful EM field produced by the wireless charger or by other conditions (e.g., short circuits). The rectifier 112 provides direct current to the linear battery charger 116, which charges the battery 118 of the implantable device 102.

The implantable device controller 120, which can control the function of the implantable device 102 as well as perform methods and tasks described herein, receives inputs from the rectifier 112, the linear battery charger 116, and the implantable device communication device 122. The implantable device controller 120 can use these inputs to estimate a present EM field value and a target EM field value. The present EM field value represents the EM field experienced at the receiving coil 138. The target EM field value represents the EM field value needed or desired to charge the battery 118. The methods and processes for determining the present EM field value and the target EM field value are discussed below with reference to FIGS. 5 and 6.

Finally, the implantable device communication device 122 is configured to communicate over a communication channel (e.g., the communication channel 110) with a charger communication device 124, to convey the present and target EM field values as well as other data or information relating to alignment or function of the implantable device 102. For example, the implantable device communication device 122 can include a transceiver capable of receiving and transmitting data with the charger communication device 124 and/or other communication devices. In some examples, the implantable device communication device may be a BLE antenna, or other shot-range communication antenna.

In one example, the implantable device controller 120 and/or the charger controller 106 may include a processor or processors. The processor includes a computer-readable medium, such as a random access memory (RAM) coupled to the processor. The processor executes computer-executable program instructions stored in memory, such as executing one or more computer programs. Such processors may include a microprocessor, a digital signal processor (DSP), an application-specific integrated circuit (ASIC), field programmable gate arrays (FPGAs), and state machines. Such processors may further include programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may include, or may be in communication with, media, for example non-transitory computer-readable storage media, that may store instructions that, when executed by the processor, can cause the processor to perform the processes described herein as carried out, or assisted, by a processor. Examples of non-transitory computer-readable media may include, but are not limited to, an electronic, optical, magnetic, or other storage device capable of providing a processor, such as the processor in a web server, with computer-readable instructions. Other examples of media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may include code for carrying out one or more of the methods (or parts of methods) described herein.

As introduced herein, the wireless charging control system 101 shown in FIG. 3 also includes the wireless charger 104 including the charger controller 106. The blocks shown within the dashed lines making up the implantable device 102 and/or the wireless charger 104 represent elements or objects typically contained within each respective component. Each component of the implantable device 102 and the wireless charger 104 are simplified and represented by individual blocks or elements though each may include multiple parts or components and/or one physical object or component may perform tasks or functions associated with one or more blocks. It should be appreciated, however, the because certain components are shown within a common dashed boundary, there is no requirement that such components be part of the same physical device. Rather, the components of the implantable device or the wireless charger 104 may be incorporated into one or more separate devices. For example as shown in FIG. 1, the charger controller 106 and the wireless charger 104 may be separate discrete devices.

The wireless charging control system 101 is shown as a simplified block diagram including components typically contained within the implantable device 102 such as the receiving coil 138, rectifier 112, overvoltage protection shunt 114, battery 118, linear battery charger 116, implantable device controller 120, and implantable device communication device 122. The charger communication device 124 is in communication with the charger controller 106 to communicate with the implantable device 102 (e.g., via the implantable device communication device 122). For example, such information can relate to the present and target EM field values, alignment data, or other information from the implantable device 102.

The wireless charger 104 also includes a power management system 126 and a EM field driver 128. The power management system 126 is configured to regulate power or electrical current flowing to the EM field driver 128 and the transmitting coil 140. The EM field driver 128 is configured as an inductive single-coil or multi-coil charger. In some examples, the EM field driver 128 and wireless charger 104 may be a wireless charger following a standard known to those in the art. In some other examples, the standards may include or be similar to a Qi inductive standard, A4WP standard, PMA standard, or any other suitable standard relating to wireless charging, either with or without a standard method of field regulation. The wireless charger 104 may operate at a frequency in a range of 110-205 kHz. In other examples, the wireless charger 104 may also be a magnetic resonance charger or other form of wireless charging such as ultrasonic charging. The wireless charger 104 may be powered by a power source 130 such as a battery or other power source such as a USB-c or other corded power supply.

The charger controller 106 is configured to control or alter electrical signals or power going to the power management system 126. For example, the charger controller 106 may increase or decrease a current flow at or through the power management system 126. For example, the charger controller 106 may instruct the power management system 126 to provide a greater or lesser level of electrical current to a EM field driver 128. The change in electrical current directed to the EM field driver 128 causes a EM field produced by the EM field driver 128 to increase or decrease in strength.

Figure 4:
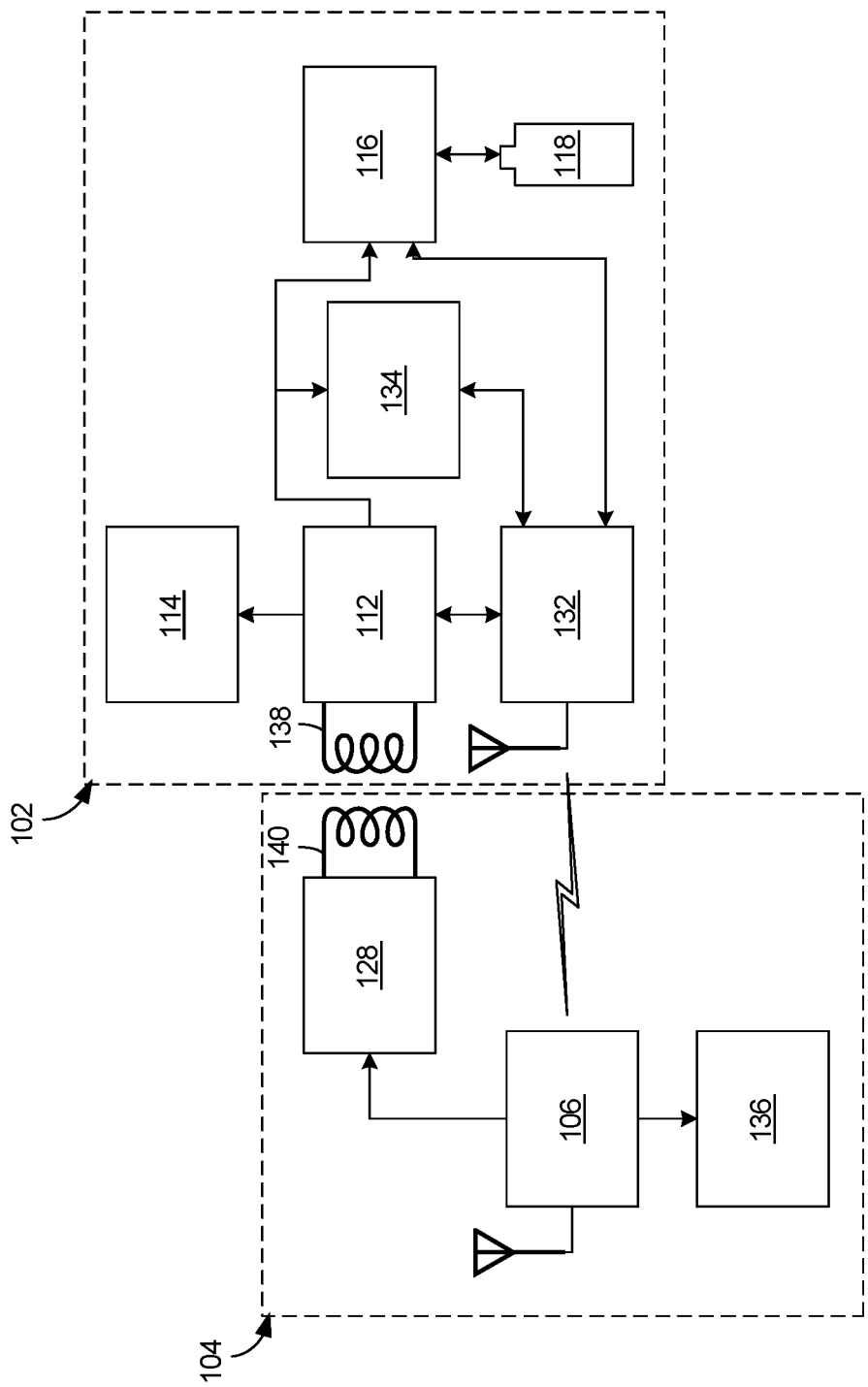
FIG. 4 illustrates a block diagram depicting a wireless control system of a wireless charging system, according to at least one example.

FIG. 4 shows an example wireless charging control system 101, according to at least one example. In this example, the implantable device 102 includes similar elements to those described above with respect to FIG. 3, including an overvoltage protection shunt 114, a rectifier 112, a receiving coil a linear battery charger 116, a battery 118. FIG. 4 also shows the implantable device 102 including an electronic load 134 which may be the circuitry, programming, processors, or other components to implement a primary function of the implantable device 102 such as neuromodulation. The implantable device 102 also includes a field estimator 132, which may also be configured with a communication capability, or may communicate with a communication device 122 as described above.

The field estimator 132 may be part of the implantable device controller 120 described above, or may be a separate component. In one example, the field estimator 132 is functionally carried out by a portion of an implantable device controller 120 to avoid introduction of additional components or elements into the implantable device 102. The field estimator 132 uses current values and voltage values from the rectifier 112 or other components of the implantable device 102 to estimate a present EM field value representing a strength of the charging EM field at the receiving coil 138. The field estimator 132 further uses a voltage of the battery 118, a present battery voltage, and a charging current value to estimate a target EM field value representing a target strength of the charging EM field, such as a charging EM field value at the receiving coil 138. The wireless charger 104 with a charger controller 106 is configured to control the EM field driver 128 to change the EM field strength and cause the present EM field value to approach and/or equal the target EM field value at the receiving coil 138. In some examples, this may achieved through continuous feedback and input from the field estimator 132. The feedback and input from the field estimator may be received or transmitted at varying rates, for example in some instances the feedback may be transmitted from the implantable device communication device at a rate of about 10 samples/second. Other sample rates are contemplated and will be understood and appreciated by those of skill in the art. In some examples, the sample rate may range from about 100 samples/second to several seconds per sample. The charger controller 106 may also include the power management system 126 described in FIG. 3 above.

The charger controller 106 is also configured to carry out alignment processes based on the data received from the field estimator 132. In particular, the charger controller 106 is configured to compare a current level flowing via the EM field driver 128 to transmitting coil 140 with a present EM field value at the receiving coil 138 as estimated by the field estimator 132. The charger controller 106 is further configured to use this comparison to extrapolate whether the wireless charger 104 can produce a EM field resulting in a present EM field value at the implantable device 102 at least equal to the target EM field value. The charger controller 106 is configured to make the extrapolation based on the current location of the wireless charger 104 and a maximum or threshold current compared to a present current delivered to the EM field driver 128. This may serve as part of an alignment system for the wireless charger 104 and the implantable device 102, to ensure proper alignment for efficient charging. When the wireless charger 104 is capable of producing the field as described above, the wireless charger 104 may be considered substantially aligned with the implantable device 102.

For example, the wireless charger 104 also includes a notification device 136 to provide a notification to a user of the system either that the wireless charger 104 is in a location or position appropriate for charging. The notification device 136 may also inform the user that the location or position is not appropriate for charging, or to continue to move the wireless charger 104 to find an appropriate location. In some instances, the notification device may indicate to the user that a current location may be adequate for a "best effort" charging mode described below but may not be adequate to provide a EM field resulting in the target current and voltage at the rectifier of the implantable device 102.

Figure 5:
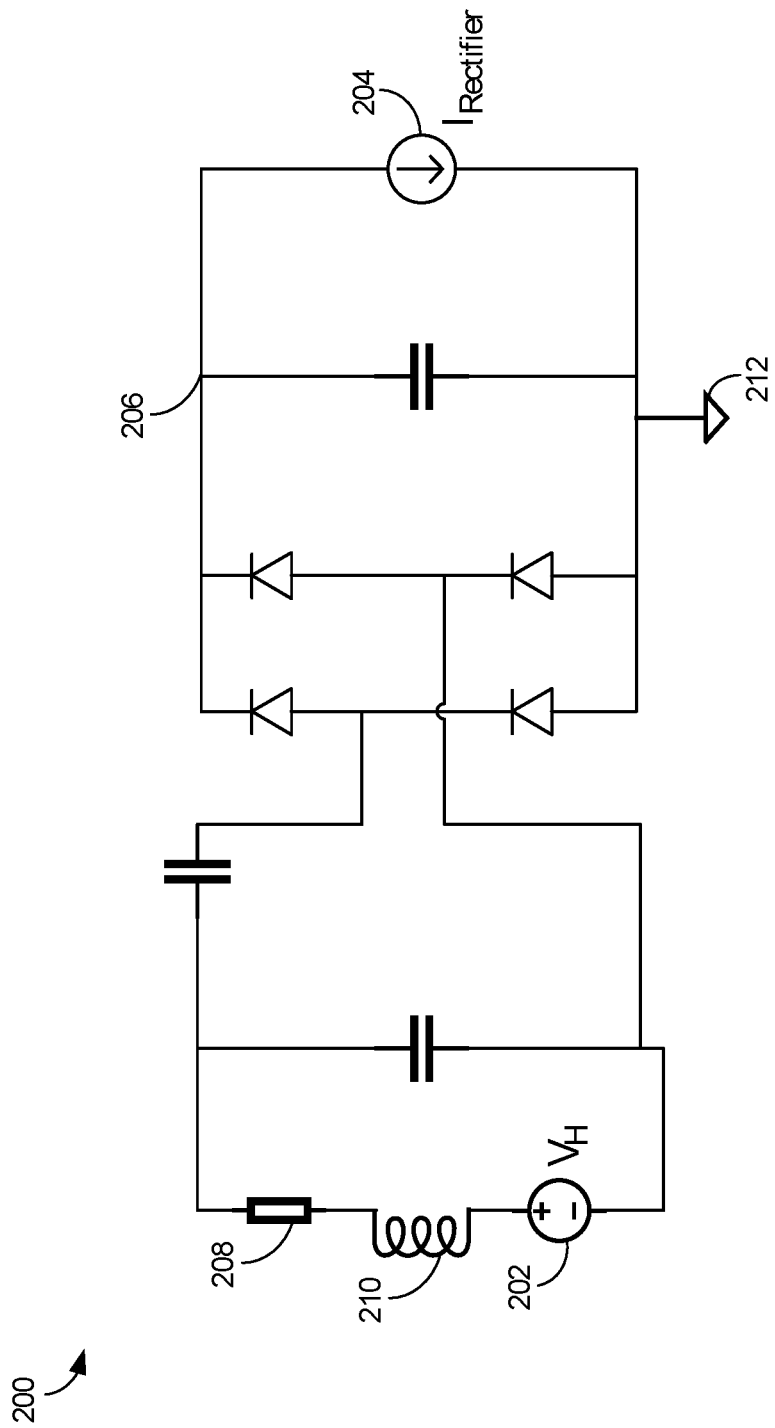
FIG. 5 illustrates an electrical model of an implantable device, according to at least one example.

FIG. 5 shows a simplified electrical model 200 of an implantable device 102 that may be used to determine the present EM field value as described above, according to at least one example. The electrical model 200 is a simplified model of the implantable device 102 showing a representative voltage source 202 to represent a voltage induced in the receiving coil 138, a coil 210 for the inductance of the receiving coil 138, and a resistor 208 for the resistance of the receiving coil 138. The electrical model is simplified, and therefore does not represent every component of the implantable device but serves to provide a simplified model which can be used to calculate the value of the representative voltage source 202. The value $V_H$ is related to the magnetic field (often represented as the vector H), and is associated with the representative voltage source 202 is directly proportional to the intensity of the EM field coupled to the receiving coil 138. $V_H$ therefore serves as a variable representative of the intensity of the EM field, sometimes referred to as the received EM field intensity, received by the receiving coil 138 which is the same field produced by the EM field driver 128. The value of $V_H$ may be determined by any method or technique typically used to resolve or solve for unknown values within circuits. For example, the Node-voltage method and mesh-current method may be used to analyze the simplified electrical model 200.

Some components of the electrical model 200 represent other components of the implantable device, such as the rectifier 112. A voltage value associated with the rectifier 112 may be measured or detected between a location 206 and the signal ground 212. Additionally, the current source 204 represents the current $I_{rectifier}$ at or through the rectifier 112. $I_{rectifier}$ may include or be determined based on a battery current and an overvoltage protection shunt current, the former representing the current flow at the battery 118 and the latter representing a current flow to the overvoltage protection shunt 114. The value of $I_{rectifier}$ may be determined by any method or technique typically used to resolve or solve for unknown values within circuits. For example, the Node-voltage method and mesh-current method may be used to analyze the simplified electrical model 200. Some signals, such as the battery current, shunt current, and rectifier voltage may be known signals within the implantable device 102, and already be monitored, measured, or otherwise known by the implantable device controller 120, e.g., for maintenance or monitoring of the implantable device. One benefit of using the electrical model 200 to determine $V_H$ as a representation of the EM field strength is that no additional components must be added to the implantable device 102, thereby maintaining as small of a footprint as possible.

The electrical model 200 may be used directly or indirectly with the known signals rectifier current and rectifier voltage to determine $V_H$. The electrical model may be input into a software program or otherwise programmed into memory to provide continuous monitoring and output of $V_H$ based on the instantaneous and/or historical data for the rectifier voltage and current. In some examples, the electrical model 200 may be used to generate data sets or tables of $V_H$ values for various combinations of rectifier voltage and current. For example, the electrical model 200 may be used to generate a Simulated Program with Integrated Circuit Emphasis (SPICE) simulation to generate data which may be used with the systems and methods described herein. In other examples, experimental observation and/or analytical methods may provide a model or data for use with the methods and systems herein.

Figure 6:
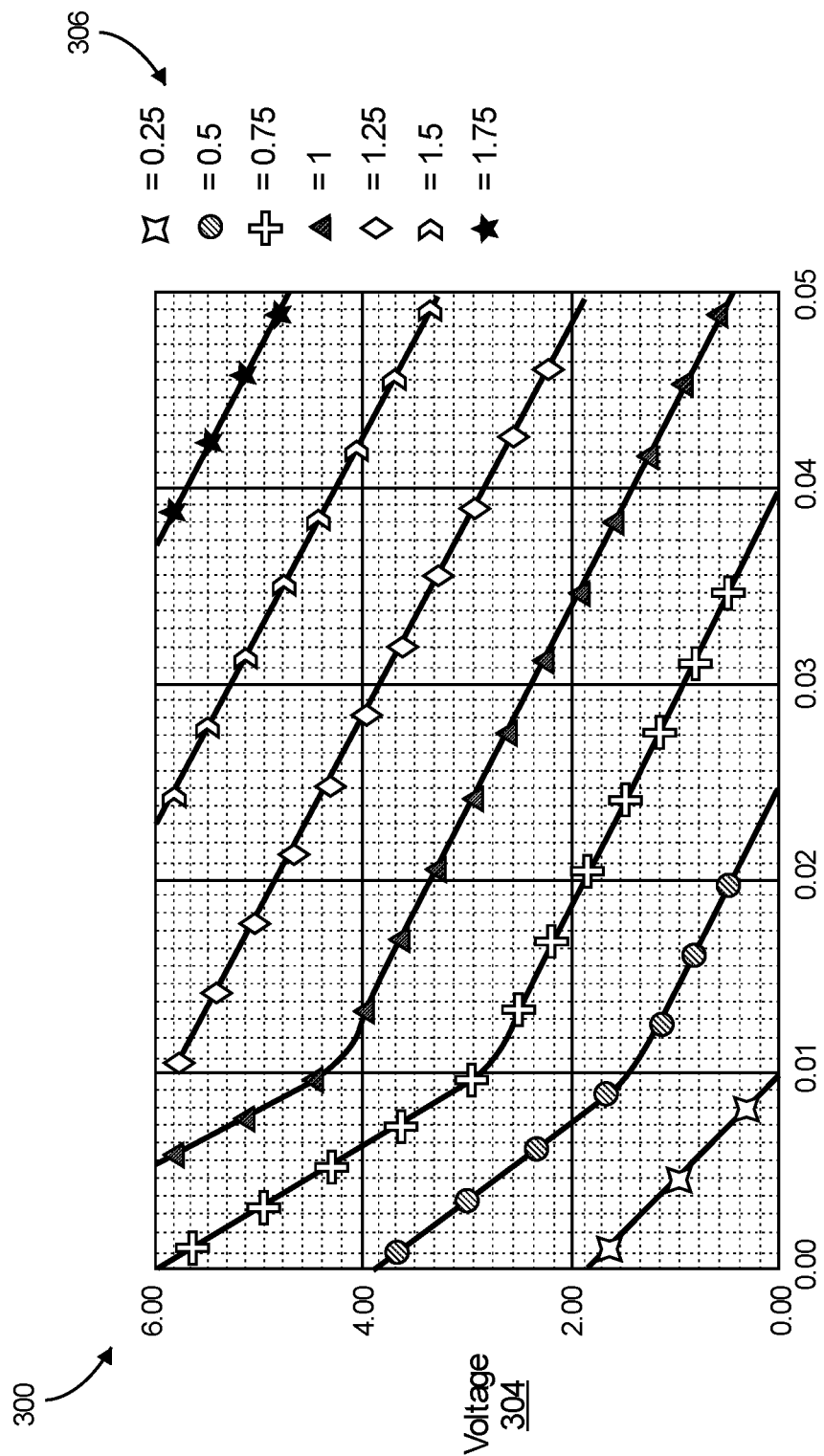
FIG. 6 illustrates a chart representative of data from the electrical model of FIG. 5, according to at least one example.

FIG. 6 shows a chart 300 displaying data representing $V_H$ as a result of rectifier current 302 and rectifier voltage 304 values, according to at least one example. The data displayed in the chart 300 is generated or computed using the electrical model 200 of FIG. 5. For example, using known capacitance, resistor, and inductance values for the additional elements of the electrical model 200, varying values of $I_{rectifier}$ at the current source 204 and voltage at location 206 are input to the model and used to solve for $V_H$ values. Each line or data set 306 is associated with a different estimated $V_H$ value. Estimating or determining $V_H$ may be performed by one or more processors of the implantable device, such as the implantable device controller 120. In some examples, the estimated $V_H$ value representing the present EM field value is conveyed to the wireless charger 104 rather than raw data. Additionally, target EM field data (described below) is conveyed rather than raw data to allow interchangeability of wireless chargers. For example, by conveying only a scalar representing a EM field strength and a scalar representing a target EM field strength, any charger may be outfitted with a controller to adjust or control the EM field driver 128.

The electrical model 200 and the chart 300 are also used to determine or estimate a target EM field value $V_{HTarget}$. The electrical values used to determine $V_{HTarget}$ include a present voltage of the battery 118, an overhead voltage (which may be static or dynamic), and a charging current. The overhead voltage and charging current may be predetermined or previously selected based on desired charging parameters. After gathering the rectifier voltage 304 and rectifier current 302 parameters, the same data, chart, or model may be used by the field estimator 132 to determine or estimate $V_{HTarget}$.

After the field estimator 132 estimates $V_H$ and $V_{HTarget}$, the implantable device communication device 122 conveys or transmits the $V_H$ and $V_{HTarget}$ values to the charger communication device 124 and the charger controller 106. The charger controller 106 uses the $V_{HTarget}$ and $V_H$ values with a conventional control architecture or system to control the inputs to the EM field driver 128.

Figure 7:
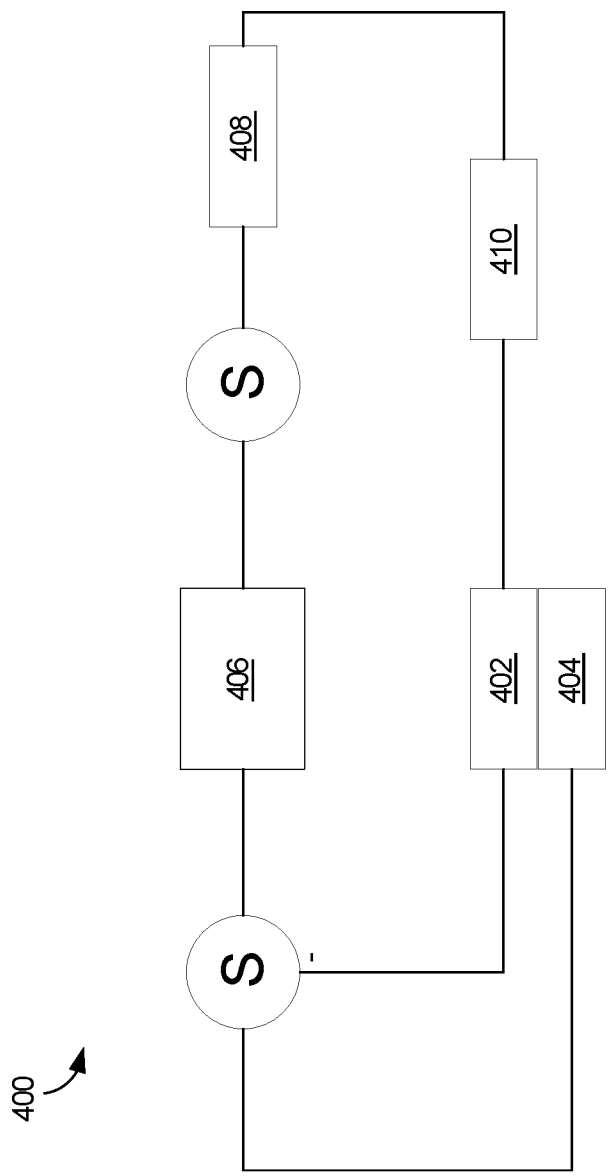
FIG. 7 illustrates a block diagram of a control system for an implantable device charger, according to at least one example.

FIG. 7 is an example controller 400 that may be used with the systems and methods described herein. The controller 400 is an example of the controller 106 The controller 400 is structured and implemented as conventional controllers are within the system. The inputs to the control portion 406 include $V_{HTarget}$ 402 and $V_H$ 404. $V_{HTarget}$ is the desired set point of the controller, with $V_H$ as the measured process value. The difference between $V_{HTarget}$ and $V_H$ is an error value to which the control portion 406 applies proportional, integral, and derivative correction terms in the case of a proportional, integral, and differential controller ("PID"). The control variable output by the control portion 406 passes through a saturation block 408 to ensure the output is limited to the possible range of control variables. The control variable determines or controls a current level passing from the power source 130 to the EM field driver 128. At block 410, the wireless charger 104 produces the EM field 108 using the controlled current level described above and the new $V_{HTarget}$ and $V_H$ values are fed into the controller 400 continuously. Although a PID controller has been described above, other control systems may be implemented in place of the controller shown in FIG. 7, including neural networks, proportional, proportional-integral, derivative, integral, or any other suitable control system available.

The controller 400 described above may be implemented as a standalone unit, or may be contained within or connected to a wireless charger. The controller 400 may provide signals to a wireless charger to alter a current or voltage supplied to the EM field driver. In other examples, the controller 400 may directly limit, increase, decrease, or otherwise control the current or voltage supplied to the EM field driver. In any of the embodiments or examples described herein, the charger controller 106 is to be understood to include both the standalone controller 400 in communication with the wireless charger as well as the wireless charger with the controller 400 integrated or connected thereto.

The systems described above, or comparable or otherwise equivalent systems or structures apparent to those with skill in the art may carry out a number of processes or methods.

Figure 8:
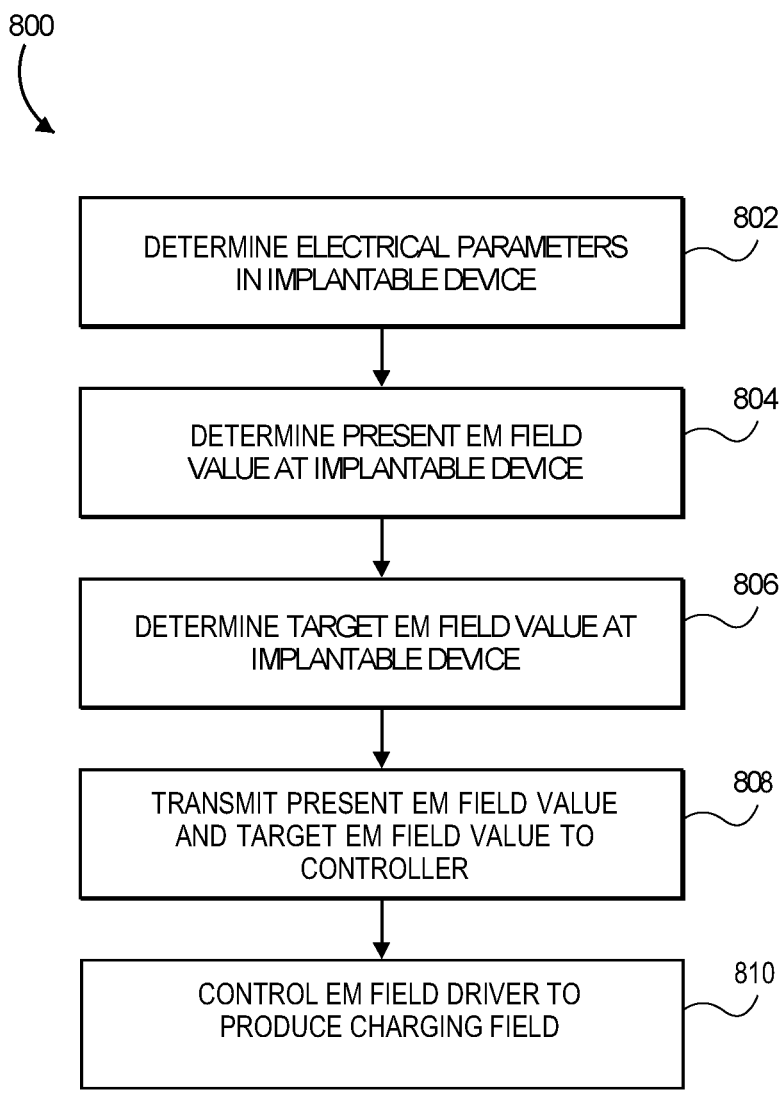
FIG. 8 illustrates an example process for controlling a charger for an implantable device, according to at least one example.
Figure 9:
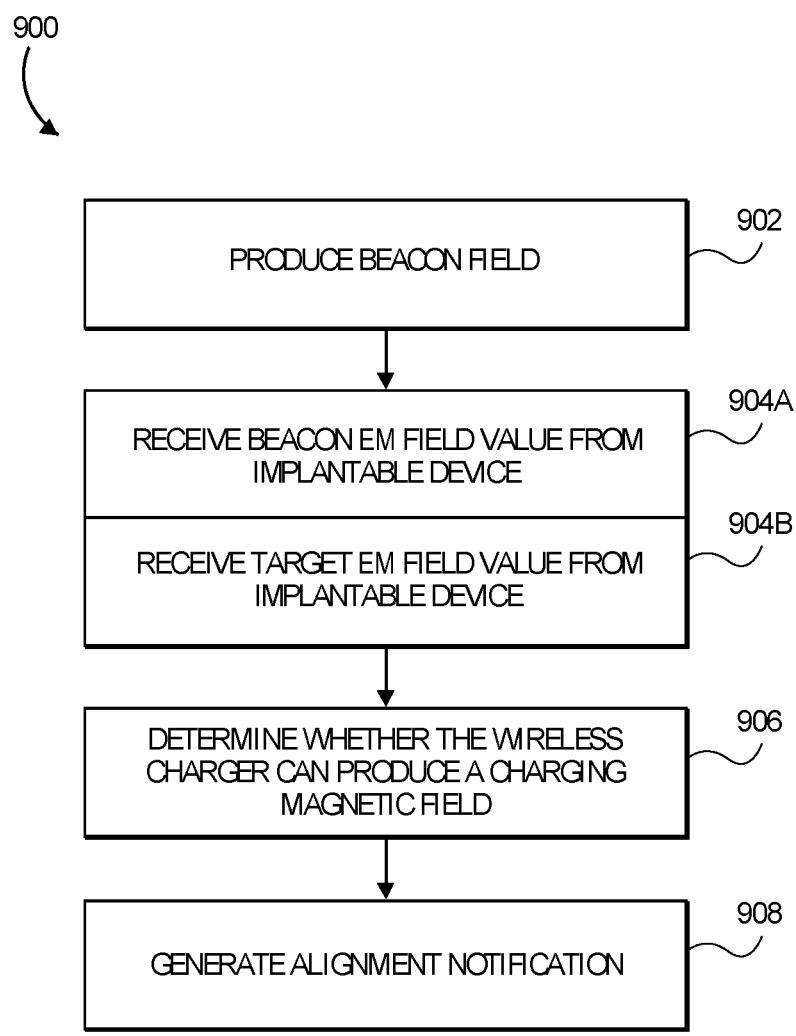
FIG. 9 illustrates an example process for aligning a wireless controller and an implantable device for charging, according to at least one example.

FIGS. 8 and 9 illustrate example flow diagram showing processes 800 and 900, according to this specification. These processes, and any other suitable processes described herein, is illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer readable storage medium, for example, in the form of a computer program including a plurality of instructions executable by one or more processors.

FIG. 8 shows a block diagram outlining the process 800 for controlling a wireless charging system, according to at least one example. The process begins at block 802 with the controller of the implant measuring or otherwise detecting electrical parameters of the implantable device 102. In some examples, the implantable device controller 120 measures or otherwise detects the electrical parameters of the implantable device 102. In some examples, the implantable device controller 120 may be directly connected to the rectifier 112 to detect or determine the electrical parameters, such as the current and voltage, at the rectifier 112. In some other examples, the implantable device controller may be connected to voltage and current sensors which measure or determine the current and voltage at the rectifier 112. Some of the parameters that may be determined or measured include, for example, the battery voltage, battery charging current, battery voltage overhead, shunt current, battery current, and rectifier voltage.

At block 804, the process 800 estimates a present EM field value at the implantable device. In some examples, the implantable device controller 120 estimates the present EM field value using a software module, data table, table of information or data, chart, or electrical model as described above. For example, the implantable device controller may include a field estimator which uses a simplified electrical model, such as the one in FIG. 5 and implement a circuit analysis such as the mesh current method, node-voltage method, or any other suitable method known to those in the art for doing circuit analysis. In some other examples, the field estimator 132 estimates the present EM field value using software modules and/or other methods described herein. In some examples, the present EM field value is estimated at the receiving coil 138. The present EM field value may include, for example, a scalar that represents the magnitude of the EM field 108 at the receiving coil 138.

At block 806, the process 800 includes determining the target EM field value at the implantable device 102. In some examples, the implantable device controller 120 and/or the field estimator estimates the target EM field value using software, data tables, charts, or electrical models as described above. For example, the implantable device controller may include a field estimator which uses a simplified electrical model, such as the one in FIG. 5 and implement a circuit analysis such as the mesh current method, node-voltage method, or any other suitable method known to those in the art for doing circuit analysis. In some examples, the target EM field value may be determined or calculated by detecting a voltage of the battery 118 and adding a charging overhead, which may be predetermined. The target EM field value represents a target magnitude of the EM field 108 at the receiving coil 138. The target EM field value is based on the desired charging parameters of the battery 118 which may be predetermined and include the charging current and the battery overhead voltage. The voltage of the battery 118 is also used to determine the target EM field value. The implantable device controller 120 estimates the $V_{HTarget}$ value using methods described above. Blocks 804 and 806 may be interchanged, to be performed in a reverse order in some examples. Additionally, blocks 804 and 806 may be performed by the implantable device controller simultaneously.

At block 808, the process 800 includes transmitting the present EM field value and the target EM field value to a controller of a wireless charger (e.g., the charger controller 106) for controlling the EM field driver to produce a charging field. The transmission from the implantable device to the controller may be accomplished via short range communications such as BLE.

At block 810, the process 800 includes controlling the EM field driver to produce a charging field. In some examples, the charger controller 106 controls or regulates the current and/or voltage supplied to the EM field driver 128. The target EM field value and the present EM field value, $V_{HTarget}$ and $V_H$ are used to control the EM field driver 128. Block 808 may include multiple sub-processes. For example, the implantable device controller 120 conveys, via the implantable device communication device 122, $V_{HTarget}$ and $V_H$ to the charger communication device 124 and the charger communication device 124 conveys $V_{HTarget}$ and $V_H$ to the charger controller 106 to control the EM field driver 128.

The process 800 is an iterative process repeatedly performed either at the initiation or throughout a charging cycle. The $V_{HTarget}$ and $V_H$ values are re-estimated, for example at a rate at or near 1 Hz, and updated at the implantable device 102 by the implantable device controller 120 and subsequently conveyed, via the implantable device communication device 122 and the charger communication device 124 to the charger controller 106 for use in controlling the current to the EM field driver 128. In some examples, the sample rate of the $V_{HTarget}$ and $V_H$ values may be faster or slower than 1 Hz, depending on the power fluctuations at the load.

FIG. 9 shows a block diagram outlining the process 900 for aligning and initiating charging of an implantable device, according to at least one example. The process 900 begins at block 902 by producing a beacon field. The beacon field is produced using a beacon current through the EM field driver 128 and transmitting coil 140. The EM field driver 128 of a wireless charger 104 produces the beacon field. The beacon field is a EM field, typically of a lower power or intensity, not intended for charging the battery of the implantable device, though a full power or intensity field is functional as well.

Block 904A, the process 900 includes receiving a beacon EM field value from the implantable device 102. The beacon EM field value is sent by the implantable device communication device 122 to the charger communication device 124. The beacon EM field value is relayed to the charger controller 106 from the charger communication device 124. The beacon EM field value is determined as described herein, and may be estimated by the field estimator 132 and/or the implantable device controller 120.

At block 904B, the process 900 includes receiving a target EM field value from the implantable device 102. The target EM field value is sent to the charger communication device 124 by the implantable device communication device 122. The charger communication device 124 relays the target EM field value to the charger controller 106. The target EM field value is determiner or estimated as described above by the field estimator 132.

At block 906, the process 900 includes determining whether the wireless charger can produce a charging EM field. The determination, made by the charger controller 106, includes whether the wireless charger 104 at its current location on the user's body can produce a EM field 108 that will cause or result in a $V_H$ at or above the $V_{HTarget}$. The charger controller 106 accomplishes this determination by comparing the beacon current to a predetermined threshold maximum current that can pass through the EM field driver 128 to produce the EM field 108 and also comparing the $V_{HB}$ with $V_{HTarget}$. The charger controller 106 determines that the wireless charger 104 may produce the desired EM field 108 when a ratio of $V_{HB}$ to $V_{HTarget}$ correlates with a ratio of the beacon current to the maximum threshold current. In some instances, other factors, such as scalar multipliers or exponentials may be used in the determination to more accurately scale between a current value and a field strength, which may not increase and/or decrease with a 1:1 proportion.

At block 908, the process 900 generates an alignment notification. If the charger controller 106 determines that a charging EM field 108 is possible at the current location at block 906, the charger controller 106 generates a notification at block 908 to a user that the implantable device 102 and wireless charger 104 are aligned for charging. The charger controller 106 may relay the notification to a notification device for alerting or notifying a user.

If, at block 906, the charger controller 106 determines that the maximum threshold current would not be capable of producing a EM field resulting in $V_{HTarget}$ then the charger controller 106 may generate a notification to the user to move the wireless charger 104 to find a better alignment position. The process 900 can be iterative to aid a user in aligning the wireless charger 104 with the implantable device 102 without requiring perfect alignment. The notification to the user to move the wireless charger may provide direction or guidance with respect to which direction to move the charger or may simply instruct the user to move the charger without further information. The guidance or direction may be in the form of a graphical user interface ("GUI") with an arrow or other indication of which direction the charger should be moved. The controller, more specifically a processor of the controller may determine the direction based on historical mapping of wireless field data as the charger has been moved on the user. For example, a user may place the charger in a first location to attempt charging, but not be in a suitable location or range for charging at that location. The charger may include location sensors, such as optical sensors, proximity sensors, gyroscopes, GPS, or other suitable sensors generally known in the art for providing location data. The user may move the charger one or many times, with the controller storing data related to the beacon EM field at each location.

In some examples, a user may attempt to align the wireless charger 104 and the implantable device 102 for a period of time without success. The charger controller 106 and/or wireless charger 104 may track locations associated with various $V_{HB}$ values as the user moves the charger seeking alignment. After a predetermined period of time, the wireless charger 104 and/or charger controller 106 may determine to enter a best effort mode for charging using the location associated with the highest $V_{HB}$. The charger controller 106 may then generate a notification through the notification device 136 instructing the user to return to the location associated with the highest Vim. In some examples, the charger controller 106 may store or instruct a computing device to store previous field values, such as $V_{HB}$.

In some examples, the notification device 136 may notify the user using a haptic notification, visual notification, audible notification, or any other suitable notification method. For example, the charger controller 106 may instruct the notification device 136 to display an arrow indicating a direction to move the charger to return to a location associated with the highest $V_{HB}$ in the best effort mode described above. The notification device 136 may provide different tones, frequency, patterns, or other modulations of notifications based on a quality of alignment. The quality of alignment may be based on the $V_{HTarget}$ and $V_{HB}$ values. For example, a $V_{HB}$ that the charger controller 106 determines will be able to produce a $V_{HTarget}$ with less current passing through the EM field driver 128 may have a higher quality of alignment and the notification device 136 may increase a frequency or a tone of audible notification based on the higher alignment quality to help a user identify a better alignment location.

The foregoing description of some examples has been presented for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

What is claimed is:

1. A system for wireless charging, the system comprising:
an implantable device comprising:
a rectifier circuit;
an electromagnetic ("EM") field receiving coil to receive a charging EM field, the EM field receiving coil electrically connected to the rectifier circuit;
a first antenna; and
a processor that iteratively performs a set of operations at a rate that is based at least in part on power fluctuations at a load, the set of operations comprising:
receiving one or more electrical signals from the rectifier circuit and a battery of the implantable device;
determining a present EM field value based on the one or more electrical signals, wherein the present EM field value includes a scalar representing a magnitude of a present EM field at the EM field receiving coil;
determining a target EM field value based on the one or more electrical signals; and
transmitting, using the first antenna, the present EM field value and the target EM field value; and
a wireless charger comprising:
a power source electrically connected to a transmitting coil to produce the charging EM field;
a second antenna that receives the present EM field value and the target EM field value from the first antenna; and
a controller that alters at least one of a voltage or a current of the power source based on the present EM field value and the target EM field value to produce the charging EM field.

2. The system of claim 1, wherein:
the processor further determines a battery voltage and a charging current based on the one or more electrical signals; and
the processor further determines the target EM field value based on the battery voltage and the charging current.

3. The system of claim 1, wherein the processor further:
determines a rectifier voltage and a rectifier current based on the one or more electrical signals; and
determines the present EM field value based on the rectifier current and the rectifier voltage.

4. The system of claim 3, wherein the processor determines the present EM field value based on an electrical model of the implantable device, the electrical model representing a relationship between the rectifier voltage, the rectifier current, and the present EM field value.

5. The system of claim 4, wherein the electrical model comprises a table of values corresponding to associated rectifier voltages, rectifier currents, and present EM field values.

6. The system of claim 1, wherein the controller receives the present EM field value and the target EM field value from the second antenna and increases an electrical current of the power source to increase the present EM field value to approach the target EM field value.

7. The system of claim 1, wherein:
the implantable device further comprises a voltage or current sensing circuit connected to the rectifier circuit that senses and transmits the one or more electrical signals to the processor; and
the one or more electrical signals comprise at least one of an output voltage or an output current from the rectifier circuit.

8. A method of charging an implantable device, the method comprising iteratively performing a set of operations at a rate that is based at least in part on power fluctuations at a load, the set of operations comprising:
measuring a set of electrical parameters of the implantable device;
determining a present electromagnetic ("EM") field value at the implantable device based on a first subset of electrical parameters of the set of electrical parameters of the implantable device, wherein the present EM field value includes a scalar representing a magnitude of a present EM field at a receiving coil of the implantable device;
determining a target EM field value at the implantable device based on a second subset of electrical parameters of the set of electrical parameters of the implantable device, the first subset of electrical parameters being distinct from the second subset of electrical parameters; and
transmitting the present EM field value and the target EM field value to a wireless charger for controlling an EM field driver of the wireless charger.

9. The method of claim 8, wherein the first subset of electrical parameters comprises a voltage and a current measured at a rectifier of the implantable device.

10. The method of claim 9, wherein the current measured at the rectifier comprises a sum of one or more electrical currents at the rectifier.

11. The method of claim 8, wherein the second subset of electrical parameters comprises a present battery voltage of a battery of the implantable device and a predetermined charging current for charging the battery.

12. The method of claim 8, wherein determining the present EM field value comprises comparing the first subset of electrical parameters with an electrical model of the implantable device comprising a relationship between the present EM field value and the second subset of electrical parameters.

13. The method of claim 12, wherein the electrical model of the implantable device comprises a table of rectifier voltages and rectifier currents and associated present EM field values.

14. The method of claim 8, wherein measuring the set of electrical parameters comprises receiving one or more signals from at least one of a current sensor or a voltage sensor.

15. A charger system, comprising:
a wireless field driver that produces an electromagnetic ("EM") field;
a signal receiver; and
a controller in communication with a wireless charger, the controller comprising:
a processor configured to execute processor executable instructions stored in a non-transitory computer-readable medium configured to cause the processor to iteratively perform a set of operations at a rate that is based at least in part on power fluctuations at a load, the set of operations comprising:
receive a present EM field value from an implantable device, wherein the present EM field value includes a scalar representing a magnitude of a present EM field at a receiving coil of the implantable device;
receive a target EM field value from the implantable device;
determine a power setting for the wireless field driver based on the present EM field value and the target EM field value; and
transmit the power setting to the signal receiver for controlling a power input of the wireless field driver.

16. The charger system of claim 15, wherein the target EM field value comprises a target value representing a target EM field intensity for charging the implantable device.

17. The charger system of claim 15, wherein the present EM field value comprises a present estimation value representing a received EM field intensity based on the EM field produced by the EM field driver.

18. The charger system of claim 15, further comprising a power regulation device in communication with the signal receiver and the wireless field driver, the power regulation device configured to regulate a power source connected to the wireless field driver in response to receiving the power setting.

19. An implantable device comprising:
an EM field receiving coil that receives a charging EM field, the EM field receiving coil electrically connected to a rectifier circuit;
a first antenna; and
a processor that iteratively performs a set of operations at a rate that is based at least in part on power fluctuations at a load, the set of operations comprising:
receiving one or more electrical signals from the rectifier circuit and a battery of the implantable device;
determining a present EM field value based on the one or more electrical signals, wherein the present EM field value includes a scalar representing a magnitude of a present EM field at the EM field receiving coil;
determining a target EM field value based on the one or more electrical signals; and
transmitting, using the first antenna, the present EM field value and the target EM field value to a second antenna of a wireless chargers.

20. The implantable device of claim 19, wherein:
the processor determines a rectifier voltage and a rectifier current based on the one or more electrical signals; and
the processor determines the present EM field value based on the rectifier current and the rectifier voltage.

21. The implantable device of claim 20, wherein the processor determines the present EM field based on a model of the implantable device, the model representing a relationship between the rectifier voltage, the rectifier current, and the present EM field value.

22. The implantable device of claim 19, wherein:
the processor determines a battery voltage and a charging current based on the one or more electrical signals; and
the processor determines the target EM field value based on the battery voltage and the charging current.

23. A computer-implemented method comprising:
iteratively performing a set of operations at a rate that is based at least in part on power fluctuations at a load, the set of operations comprising:
receiving one or more electrical signals from a rectifier circuit and a battery of an implantable device;
determining a present electromagnetic (EM) field value based on the one or more electrical signals, wherein the present EM field value includes a scalar representing a magnitude of a present EM field at a receiving coil of the implantable device;

determining a target EM field value based on the one or more electrical signals; and transmitting using a first antenna of the implantable device, the present EM field value and the target EM field value.

24. The computer-implemented method of claim 23, further comprising:

determining a battery voltage and a charging current based on the one or more electrical signals; and determining the target EM field value based on the battery voltage and the charging current.

25. The computer-implemented method of claim 23, further comprising:

determining a rectifier voltage and a rectifier current based on the one or more electrical signals; and determining the present EM field value based on the rectifier current and the rectifier voltage.

26. The computer-implemented method of claim 25, wherein determining the present EM field value is based on an electrical model of the implantable device, the electrical model representing a relationship between the rectifier voltage, the rectifier current, and the present EM field value.

27. The computer-implemented method of claim 26, wherein the electrical model comprises a table of values corresponding to associated rectifier voltages, rectifier currents, and present EM field values.

28. The computer-implemented method of claim 23, wherein receiving the present EM field value and the target EM field value from a second antenna of the implantable device increases an electrical current of a power source to increase the present EM field value to approach the target EM field value.

29. The computer-implemented method of claim 23, wherein:

the implantable device further comprises a voltage or current sensing circuit connected to the rectifier circuit that senses and transmits the one or more electrical signals; and the one or more electrical signals comprise at least one of an output voltage or an output current from the rectifier circuit.

30. One or more non-transitory computer-readable media comprising computer-executable instructions that, when executed by one or more computing systems, cause the one or more computing systems to:

iteratively perform a set of operations at a rate that is based at least in part on power fluctuations at a load, the set of operations comprising:

receiving one or more electrical signals from a rectifier circuit and a battery of an implantable device;

determining a present electromagnetic (EM) field value based on the one or more electrical signals, wherein the present EM field value includes a scalar representing a magnitude of a present EM field at a receiving coil of the implantable device;

determining a target EM field value based on the one or more electrical signals; and transmitting using a first antenna of the implantable device, the present EM field value and the target EM field value.

31. The one or more non-transitory computer-readable media of claim 30, further comprising computer-executable instructions that, when executed by one or more computing systems, cause the one or more computing systems to:

determine a battery voltage and a charging current based on the one or more electrical signals; and determine the target EM field value based on the battery voltage and the charging current.

32. The one or more non-transitory computer-readable media of claim 31, further comprising computer-executable instructions that, when executed by one or more computing systems, cause the one or more computing systems to:

determine a rectifier voltage and a rectifier current based on the one or more electrical signals; and determine the present EM field value based on the rectifier current and the rectifier voltage.

33. The one or more non-transitory computer-readable media of claim 32, wherein determining the present EM field value is based on an electrical model of the implantable device includes using the electrical model representing a relationship between the rectifier voltage, the rectifier current, and the present EM field value.

34. The one or more non-transitory computer-readable media of claim 30, wherein receiving the present EM field value and the target EM field value from a second antenna of the implantable device increases an electrical current of a power source to increase the present EM field value to approach the target EM field value.

35. The one or more non-transitory computer-readable media of claim 30, wherein:

the implantable device further comprises a voltage or current sensing circuit connected to the rectifier circuit that senses and transmits the one or more electrical signals; and the one or more electrical signals comprise at least one of an output voltage or an output current from the rectifier circuit.

* * * * *